United States Patent [19]

Rothrum

[11] Patent Number: 5,765,566
[45] Date of Patent: Jun. 16, 1998

[54] SURGICAL DRAPES HAVING TAPE ATTACHMENT STRIPS

[75] Inventor: Robert J. Rothrum, Coon Rapids, Minn.

[73] Assignee: Minnesota Mining and Manufacturing Company, St. Paul, Minn.

[21] Appl. No.: 273,500

[22] Filed: Jul. 11, 1994

[51] Int. Cl.$^6$ .......................... A61B 19/00; A61B 19/08
[52] U.S. Cl. ............................. 128/849; 128/853
[58] Field of Search .................. 128/849–856; 602/54–58, 3

[56] References Cited

U.S. PATENT DOCUMENTS

| | | | |
|---|---|---|---|
| Re. 24,906 | 12/1960 | Ulrich | 206/59 |
| 3,060,932 | 10/1962 | Pereny et al. | 128/849 |
| 3,263,680 | 8/1966 | Morgan | 128/853 |
| 3,494,356 | 2/1970 | Melges . | |
| 3,625,205 | 12/1971 | Madden | 128/822 |
| 3,695,260 | 10/1972 | Endres | 128/132 D |
| 3,741,206 | 6/1973 | Binard et al. | 128/132 D |
| 3,766,913 | 10/1973 | Balin | 128/132 D |
| 3,783,862 | 1/1974 | Schrading et al. | 128/855 |
| 3,809,077 | 5/1974 | Hansen | 128/132 D |
| 3,865,770 | 2/1975 | Blake | 260/27 R |
| 3,889,667 | 6/1975 | Collins | 128/855 |
| 3,916,887 | 11/1975 | Kelly | 128/851 |
| 3,930,497 | 1/1976 | Krebs et al. . | |
| 3,942,523 | 3/1976 | Rudtke | 128/132 D |
| 3,955,569 | 5/1976 | Krzewinski et al. | 128/855 |
| 4,067,327 | 1/1978 | Shannon, Sr. | 128/849 |
| 4,089,331 | 5/1978 | Hartigan et al. | 128/132 D |
| 4,196,723 | 4/1980 | Moose, Jr. | 128/132 D |
| 4,316,456 | 2/1982 | Stoneback | 128/132 D |
| 4,336,797 | 6/1982 | Latucca et al. | 128/132 D |
| 4,413,080 | 11/1983 | Blake | 524/187 |
| 4,524,095 | 6/1985 | Gockel et al. | 428/43 |
| 4,524,767 | 6/1985 | Glassman | 128/132 D |
| 4,561,434 | 12/1985 | Taylor | 128/132 D |
| 4,569,341 | 2/1986 | Morris | 128/853 |
| 4,569,960 | 2/1986 | Blake | 524/145 |
| 4,574,796 | 3/1986 | Lundstrom et al. | 128/132 D |
| 4,690,137 | 9/1987 | Starzmann | 128/132 D |
| 4,727,864 | 3/1988 | Wiesenthal et al. | 602/3 |
| 4,890,628 | 1/1990 | Jackson | 128/849 |
| 4,899,762 | 2/1990 | Muller | 128/850 |
| 5,019,071 | 5/1991 | Bany et al. | 604/389 |
| 5,125,995 | 6/1992 | D'Haese et al. | 156/155 |
| 5,152,282 | 10/1992 | Elphick et al. | 602/57 |
| 5,158,557 | 10/1992 | Noreen et al. | 604/389 |
| 5,270,111 | 12/1993 | D'Haese et al. | 428/356 |

FOREIGN PATENT DOCUMENTS

| | | | |
|---|---|---|---|
| 0 169 316 | 1/1986 | European Pat. Off. . | |
| 2148125 | 5/1985 | United Kingdom | 128/846 |
| WO 93/07914 | 10/1992 | WIPO | A61L 31/00 |

OTHER PUBLICATIONS

PCT Search Report for PCT/US95/06023.

*Primary Examiner*—Jessica J. Harrison
*Assistant Examiner*—Michael O'Neill

[57] ABSTRACT

The present invention provides a universal surgical drape kit, comprising: a plurality of drape panels each having a top surface and a bottom surface; and a plurality of tape attachment strips comprising a backing, an adhesive layer covering one side of said backing, and a liner. At least two of the tape attachment strips are adhesively attached to the top surface and along at least a portion of one edge of the drape panels and a second portion of the tape attachment strips overhangs the drape panels and is covered with a liner. The present invention also provides a surgical drape, comprising: a sheet of drape fabric having a rectangular fenestration cut therein; and four tape attachment strips comprising a backing, an adhesive layer covering one side of said backing, and a liner. The four tape attachment strips are adhesively attached to the top surface of the sheet along the edges of the fenestration and a second portion of the tape attachment strips overhangs the fenestration and is covered with a liner.

9 Claims, 7 Drawing Sheets

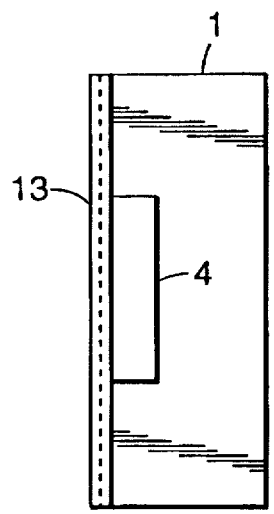 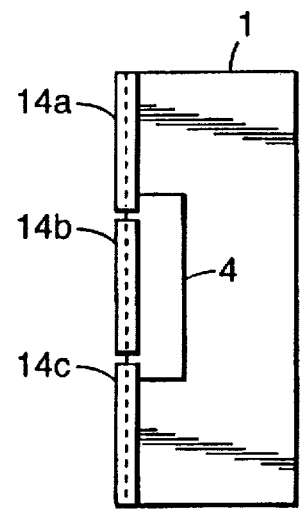
*Fig. 4*  *Fig. 5*
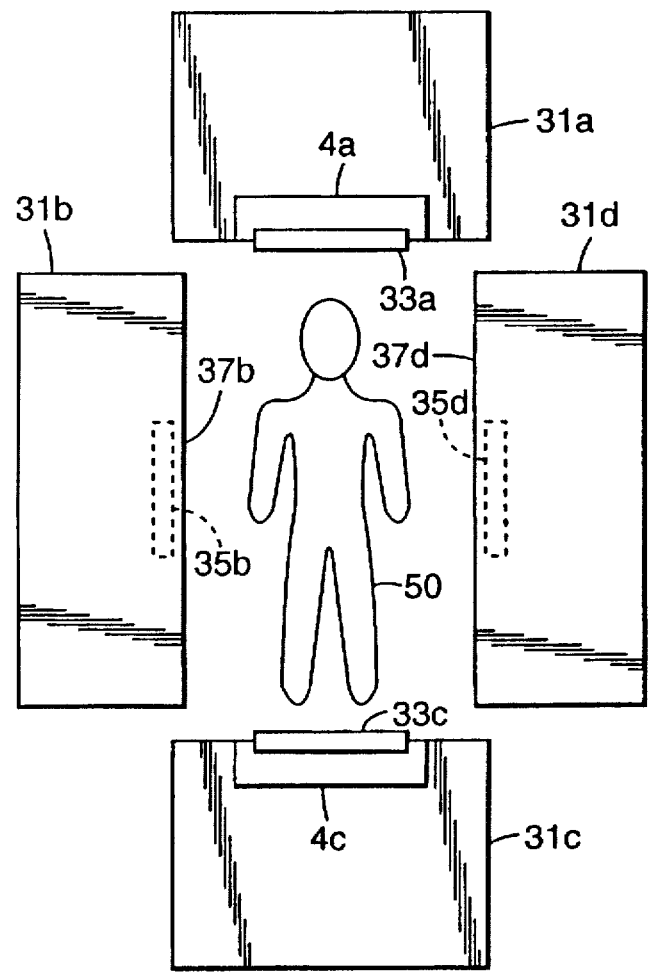
*Fig. 6a*

SURGICAL DRAPES HAVING TAPE ATTACHMENT STRIPS

FIELD OF THE INVENTION

This invention relates to novel surgical drapes having adhesive tapes which are used to assemble the drapes and/or attach the drapes to a patient. This invention also relates to a method for forming a universal surgical drape.

BACKGROUND OF THE INVENTION

A wide variety of surgical drapes having various sized openings (hereinafter referred to as "fenestrations") which provide access to the surgical site are available for use by the health care provider. The drapes can comprise simple rectangular sheets of material or can comprise elaborate shapes of material having specialized function.

In general, surgical drapes may be separated into two main classes (reusable or disposable). Reusable linen or cloth drapes are designed to be laundered after use and sterilized again for use in a subsequent operation. In some cases the reusable drape is fitted with specialized fluid collection pouches and/or incise drape materials in the operating theater. After the drape has been used, these devices are preferably removed prior to the drape being laundered. Unfortunately, the pouches or incise materials are often adhered to the reusable drape fabric and are not removed easily from the drape without leaving an adhesive residue on the drape. This adhesive residue is difficult to remove by conventional laundry procedures. Disposable drapes constitute the other class of drapes. These drapes are designed to be used once and then destroyed. A wide variety of sizes and shapes are available. Unfortunately, the large number of specialized sizes and shapes creates an inventory problem for the hospital. To lessen the inventory problem a universal draping technique has been developed using four "panels" (or "sheets") of fabric. This technique (sometimes referred to as "squaring off" the incision site)may be practiced using either reusable or disposable drape fabrics. Each panel is used to cover a portion of the patient, with the panels arranged in such a manner as to define a opening around the surgical site. While this technique lessens the number and variety of surgical drapes needed in the hospital inventory, there still exists some disadvantages to this technique that have not been adequately addressed.

Notably, when the universal drape technique is used without an incise drape material the technique fails to adequately seal the drape edge to the surgical site. As a result any fluids emanating from the surgical site are apt to flow under the drapes and create an unsanitary mess. In addition, when the universal drape technique is used with reusable linen fabrics, and an incise drape material is employed, the aforementioned laundry problem remains unsolved (i.e., the incise drape material may leave adhesive residue on the linens). It would be desired to produce a universal surgical drape and draping technique which solves these problems and is economical to produce.

SUMMARY OF THE INVENTION

The present invention provides a universal surgical drape which may be easily assembled to provide a drape with a fenestration. The universal drape preferably comprises four panels of drape material. At least two (and preferably all four) of the panels of drape material have adhesively attached, and overhanging along at least a portion of one edge of the sheet, a tape attachment strip comprising a single-sided adhesive tape. A portion of the tape attachment strip overhangs the edge of the panel and is covered with a liner. In use, the liner is removed (thus exposing an additional portion of the adhesive surface of the tape attachment strip) and the exposed adhesive is placed against the skin to which the drape is being attached and/or against the top surface of an underlying drape. This design provides a leak free perimeter seal between the patient and the top surface of the universal drape. Thus fluid is easily able to flow over the sealed region onto the universal drape without being inhibited, directed away, or causing pooling of fluid at the surgical site.

The present invention provides novel surgical drapes having tape attachment strips around a fenestration. The tape attachment strips provide a leak free perimeter seal between the patient being draped and the top surface of the drape. In addition, the tape attachment strips provide a landing surface for an optional incise drape material to be attached to (e.g., to avoid direct contact between the adhesive of the incise drape and the main drape material). The landing surface also provides a surface that the incise drape can adhere to. When the tape attachment strip comprises a water-dispersible adhesive, the drape fabric may be easily separated from the tape attachment strip during the laundry process.

The present invention also provides a method of making a panel for a universal drape comprising the steps of contacting a portion of the adhesive surface of a single-sided adhesive tape (along the long edge of the tape) to a portion of the edge of a drape panel along its top surface, and covering the unexposed portion of the adhesive surface of said single-sided adhesive tape with a liner.

RELATED APPLICATIONS

Of related interest is U.S. Patent Application "Surgical Fluid Collection Pouch". Ser. No. 08/273,598, filed on even date herewith by the assignee of this invention, which is herein incorporated by reference.

BRIEF DESCRIPTION OF THE DRAWINGS

FIG. 1a illustrating a four panel universal drape prior to assembly, FIG. 1b illustrating the same drape after assembly;

FIGS. 2a, 2b, and 2c are alternative cross-sectional views of the universal surgical drape of the present invention taken along line 2—2 of FIG. 1a;

FIGS. 4 and 5 are alternative top plan views of one panel of a universal drape of the present invention;

FIGS. 6a and 6b are alternative top plan views of a universal surgical drape of the present invention, FIG. 6a illustrating a four panel universal drape prior to assembly, FIG. 6b illustrating the same drape after assembly;

DETAILED DESCRIPTION OF THE INVENTION

Figure 1A:
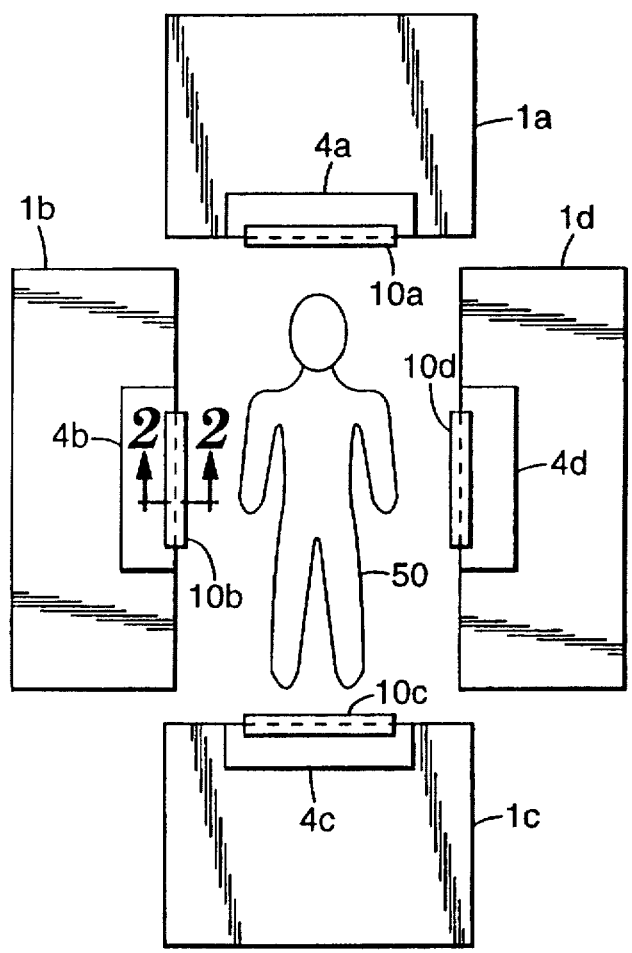
FIGS. 1a and 1b are top plan views of a universal surgical drape of the present invention.

In a first embodiment, the present invention provides a universal surgical drape comprising a plurality of drape panels wherein at least two panels, and more preferably four panels, comprise a tape attachment strip having a backing, an adhesive layer covering one side of the backing, and a liner. A portion of the tape attachment strip is adhesively attached along at least a portion of one edge of the panel and wherein the liner covers that portion of the adhesive layer which is not attached to the panel.

Tape attachment strips (comprising a backing, an adhesive layer coated on one side of the backing, and a liner) are used to assemble the universal drape and also to attach the universal drape to a patient, thus defining a fenestration around a surgical site. The tape attachment strips provide a "ramped" transition between the patient being draped and the top surface of the universal drape. As a result, fluids are able to flow readily over the ramp and onto the top surface of the drape (where they are absorbed or collected, e.g., into a fluid collection pouch).

The tape attachment strips allow for great flexibility and economy for the user. Drape panels which comprise the tape attachment strip may be positioned easily and assembled to form a variety of custom fitting universal surgical drapes. This allows the health care provider to form a "customized" drape (suitable for many different surgical procedures) that fits many different size patients or has many different sized fenestrations. As a result, fewer styles of specialized drapes (e.g., sized drapes which incorporate fixed sized fenestrations) must be inventoried by the hospital.

In addition, the tape attachment strip described herein provides a cost effective method whereby a drape manufacturer can easily assemble universal drape kits. The tape attachment strip of the present invention is compatible with most drape materials and can easily be cut to size and assembled into the finished universal drape. The tape attachment strip preferably comprises a slit liner, thus facilitating easy attachment of the tape to the drape fabric. In use, a first portion of the liner is removed (thus exposing a strip of adhesive along the length of the tape) and the exposed portion of adhesive is placed against the drape fabric to which the tape attachment strip is being attached. This technique avoids the necessity of maintaining precise alignment of the tape to the edge of the drape fabric.

In a preferred embodiment, the tape attachment strip comprises a "single-sided" pressure sensitive adhesive tape (i.e., a tape comprising a backing and a pressure sensitive adhesive, i.e., "PSA", coated on one side of said backing) which is partially affixed at least to a portion of the edge of the drape panel (i.e., to that portion of the edge of the panel which forms the fenestration of the assembled universal drape). This leaves a portion of the single-sided adhesive tape free for attachment to the surface to which the drape is being attached. The free portion of adhesive tape is preferably protected, prior to use, with a liner. The liner may be easily peeled away from the tape to expose the adhesive.

Suitable single-sided adhesive tapes for use in the present invention include commercially available single-sided medical tapes. For example, No. 1523 tan 0.13 mm polyethylene medical tape; No. 1526 transparent 0.13 mm polyethylene medical tape; No. 9830 transparent 0.07 mm polyethylene medical tape; No. 9833 white 0.14 mm polyethylene medical tape; and No. 9838 white medical tape having a paper backing and a water-dispersible adhesive are suitable for use in the present invention with disposable drapes. No. 9838 white medical tape is suitable for use in the present invention with reusable drapes. Nos. 1523, 1526, and 9830 medical tapes have matte finishes on the non-adhesive surface. All of the tapes are coated on one surface with a hypoallergenic, pressure sensitive acrylate adhesive and are wound with a bleached Kraft paper liner (preferably slit lengthwise) having a silicone-treated, polyethylene coated surface. The liner (or a portion of the liner) may be separated from the tape during application of the tape to the drape panel. All of the above-identified commercially available tapes are available from Minnesota Mining and Manufacturing Company of St. Paul, Minn., U.S.A. Most of these medical tapes are identified in *3M Medical Specialties Product Reference Guide* published by 3M Health Care in 1991 and available from 3M Medical Specialties Department, the disclosure of which is incorporated by reference herein. The remainder of these medical tapes are also available in publications from 3M Medical Specialties Department.

Suitable adhesives for use in the present invention include those pressure sensitive adhesives which are capable of providing the necessary amount of peel strength and/or shear strength to function in the manner required (e.g., sufficient strength to attach securely the drape panels to the patient without unintended detachment). Preferred adhesives for use in the medical field should be non-toxic, more preferably hypoallergenic, and are most preferably also environmentally safe.

Suitable pressure sensitive acrylate adhesives for use in the present invention include, for example, copolymers which are reaction products of the polymerization of at least one "A" monomer and at least one "B" monomer to yield a copolymer having an inherent viscosity of about 1.0 dl/g to about 2.0 dl/g. The A monomer is a polymerizable monomer comprising an acrylate or methacrylate ester of a non-tertiary alcohol or a mixture of non-tertiary alcohols with the alcohols having from 1 to 14 carbon atoms and desirably averaging about 4 to 12 carbon atoms. The B monomer is an ethylenically unsaturated compound and desirably may be acrylic acid, methacrylic acid, itaconic acid, acrylamide, methacrylamide, acrylonitrile, methacrylonitrile, vinyl acetate, N-vinyl pyrrolidone, or combinations thereof. The A monomer is polymerizable and contributes the viscoelastic properties of the pressure sensitive adhesive copolymer. Non-limiting examples of such A monomers include the esters of acrylic acid or methacrylic acid with non-tertiary alkyl alcohol such as 1-butanol, 1-pentanol, 2-pentanol, 3-pentanol, 2-methyl-1-butanol, 1-methyl-1-butanol, 1-methyl-1-pentanol, 2-methyl-1-pentanol, 3-methyl-1-pentanol, 2-ethyl-1-butanol, 2-ethyl-1-hexanol, 3,5,5-trimethyl-1-hexanol, 3-heptanol, 2-octanol, 1-decanol, 1-dodecanol, and the like. Such monomeric acrylic or methacrylic esters are known in the art, and many are commercially available. The B monomer is an ethylenically unsaturated compound copolymerized with the A monomer to affect the physical properties of the resulting pressure sensitive adhesive copolymer. In general, the presence of the B monomer will reduce the flexibility of the resulting pressure sensitive adhesive copolymer. Thus, the weight percentages of the A monomer and the B monomer should be balanced in order to provide a pressure sensitive adhesive copolymer having an inherent viscosity of from about 1.0 dl/g to about 2.0 dl/g. The weight percentage ratio of A monomer: B monomer ranges from about 85:15 to about 98:2 and desirably from about 90:10 to 97:3.

The pressure sensitive adhesive copolymer should be tacky at room temperature as well as at skin temperature of mammals. Also, the adhesive should be hypoallergenic, i.e., after continuous contact with skin, there is no significant skin sensitization or irritation during adhesion. Often, to determine if an adhesive is hypoallergenic, the following evaluations are conducted: cell cytotoxicity, skin irritation, and sensitization potential. The United States Food and Drug Administration recommends such evaluations in a Tripartite Biocompatibility Draft Guidance for Medical Devices. The commercially available medical tapes described herein using acrylate pressure sensitive adhesives of the type described herein are generally considered hypoallergenic. Presently preferred as an acrylate pressure sensitive adhesive for tapes used in the present invention is an isooctyl acrylate/acrylic acid copolymer in a weight ratio of about 94:6. The inherent viscosity of the copolymer is about 1.4–1.6 dl/g. Preferably, acrylate pressure sensitive adhesives have a tackifier added to the formulation to improve tack. Commercially available tackifiers include, for example, "Foral" branded colophony acid rosins, such as "Foral AX" and "Foral 85" rosins, commercially available from Hercules Corporation, and partially hydrogenated methylstyrene hydrocarbon resins, such as "Piccolastic A25" resin, also commercially available from Hercules Corporation. Such tackifiers can be added during preparation of the acrylate pressure sensitive adhesive in an amount of about 35–40 weight percent of the copolymer solids.

Alternate pressure sensitive adhesives useful in the present invention include, for example, hypoallergenic Kraton rubber-based pressure sensitive adhesives produced using styrene-butadiene or styrene-isoprene copolymers commercially available as Kraton branded copolymers from Shell Oil Company of Houston, Tex. A variety of Kraton based pressure sensitive adhesives are disclosed in U.S. Pat. Nos. 5,019,071 (Bany et al.) and 5,158,557 (Noreen et al.), the disclosures of which are incorporated by reference herein. Preferred as Kraton rubber-based pressure sensitive adhesives are Kraton 1107, Kraton 1111, Kraton 1101, and Kraton D branded copolymers, tackified with compatible tackifiers such as Escorez™ 1310LC branded tackifier commercially available from Exxon Chemicals, a solid $C_5$ tackifying resin commercially available as Wingtack™ Plus brand tackifier from Goodyear Tire and Rubber Company, Akron, Ohio and naphthenic oils having 10% aromatics commercially available as Shellflex™ 371 from Shell Oil Company. Such tackifiers can comprise about 45 to about 70 weight percent of the pressure sensitive adhesive, while the Kraton copolymer can comprise about 30 to 55 weight percent. Presently preferred is a Kraton based pressure sensitive adhesive comprising about 35 weight percent Kraton 1111, about 53 weight percent Wingtack Plus, about 11 weight percent Shellflex 371, and about 2 weight percent Irganox 1010 and 1076 branded antioxidants, in a similar formulation to that disclosed in Examples 1–13 of U.S. Pat. No. 5,019,071.

Additional alternate and presently preferred pressure sensitive adhesives useful in the present invention include, for example, the water-dispersible pressure sensitive adhesives disclosed in U.S. Pat. Nos. 3,865,770; 4,413,080; 4,569,960; 5,125,995; and 5,270,111 and in U.S. patent application Ser. Nos. 07/763,823; 07/889,647; and 08/093,080 the disclosures of which are herein incorporated by reference.

Pressure sensitive adhesive copolymers can be copolymerized using known polymerization techniques such as emulsion polymerization and solution polymerization. Sources of polymerization preparation and techniques include *Organic Polymer Chemistry*, Saunders et al. (Halsted Publishing Company, New York 1973); *Applied Polymer Science*, Tess et al. (American Chemical Society, Washington, D.C., 1981); *Principles of Polymerization*, Odien (John Wiley and Sons, New York, 1981); and the *Handbook of Pressure-Sensitive Adhesive Technology*, Second Edition, Satas, Ed., (Van Nostrand Reinhold Company, New York, 1989), the disclosures of which are incorporated by reference. Specifically, acrylate pressure sensitive adhesive copolymers can be prepared according to U.S. Pat. No. 2,884,126/RE 24,906 (Ulrich), the disclosure of which is incorporated by reference herein. The presently preferred acrylate copolymer pressure sensitive adhesive can be prepared by emulsion polymerization according to Example 5 of U.S. Pat. No. 2,884,126/RE 24,906, except that tackifier is added to the emulsion in an amount of about 35–40% weight percent of copolymer solids, and that tackified copolymer is dissolved in a heptane-isopropanol (70:30) solution. The presently preferred Kraton copolymer pressure sensitive adhesive can be prepared in the manner as disclosed in Examples 1–13 of U.S. Pat. No. 5,019,071, the disclosure of which is incorporated by reference above.

The adhesive surface of the tape attachment strip is preferably covered prior to use with a suitable liner. Suitable liners include any material which adequately covers the adhesive (thus preventing contamination of the adhesive tack) and which can be easily peeled apart from the adhesive. Preferred liners have a low adhesion coating (such as a silicone treated polyethylene coating) which facilitates the easy peeling apart of the liner.

More preferably, the adhesive tape is initially provided with a liner that has been slit lengthwise into at least two narrower pieces (or "strips"). A first lengthwise piece of liner is removed by the manufacturer or end user to expose a first portion of the adhesive surface. This first portion of adhesive surface is then contacted with the drape panel fabric. The second liner portion is temporarily left in place and is removed when the drape panel is to be attached to the patient. When it is desired to assemble the drape (thus forming a fenestration), the health care provider peels off the remaining portion of the liner and attaches the exposed adhesive to the patient or to an underlying drape panel.

Figure 9:
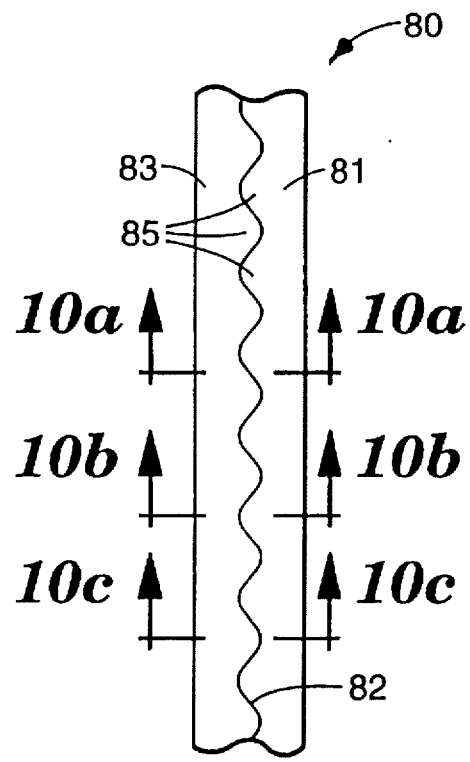
FIG. 9 is a plan view of the liner side of an alternative tape attachment strip of the present invention, wherein the liner has been slit lengthwise using a sinusoidal pattern.

The slit which separates the liner strips may be either a straight line or a curved line (e.g., a sinusoidal line) running the length of the tape. In addition, the liner may be slit into two or more equal width strips of liner or into two or more different width strips of liner. In general, a straight line slit has the advantage of being simple to produce. Alternatively, a curved line slit such as a "sinusoidal" slit has the advantage of providing integral "tabs" of liner when the tape backing is flexed along the slit line. In use, when a tape having a sinusoidally slit liner is flexed along the slit (as shown in FIGS. 9 and 10), a portion of the liner lifts away from the underlying tape. This lifted portion can then be easily grasped and the liner peeled apart from the tape.

The single-sided adhesive tape attachment strip has several advantages over double-sided adhesive tapes. Notably, single-sided adhesive tapes are generally less expensive to produce than double-sided adhesive tapes. In addition, the single-sided adhesive tape attachment strip is easy to attach at the edge of a drape panel (i.e., without the need for precise alignment) and provides a ramp over which fluids may easily flow. In contrast, double-sided adhesive tapes are difficult to align and attach precisely at the edge of a drape panel. Thus, a non-adhered portion of the drape fabric is often left exposed. This non-adhered portion can inhibit fluid flow onto the top surface of the drape.

The drape itself may be made from any number of materials (e.g., disposable or reusable materials) and combinations thereof. Breathable materials such as woven and nonwoven materials may be used in the construction of the drape. Such materials are desirable in that they are breathable and therefore allow air circulation and provide an added degree of comfort to the patient. Alternatively, a fluid impervious material such as plastic film may be used as the sheet material or a combination of nonwoven and film materials may also be used. For example, the drape, as a whole, may be made from a breathable nonwoven material and the area surrounding the fenestration may be made fluid impervious (e.g., by adding a layer of plastic film or by treating the nonwoven material with a coating of fluid impervious material) and/or fluid absorbent material (e.g., by adding a layer of absorbent material such as Drysite™ available from Johnson and Johnson Medical Inc.).

Preferred drape fabrics for use in the present invention include those fabrics described in U.S. Pat. No. 3,809,077 (Hansen); U.S. patent application Ser. No. 08/105,430; and PCT Patent Application WO 93/07914 (Weimer et al.), which are herein incorporated by reference. Suitable drape fabrics for use in the present invention also include commercially available drape fabrics such as Sontara™ (e.g., #8018) nonwoven polyester fabrics (available from E. I. Du Pont de Nemours Company and presently believed to be used in drapes made by Johnson and Johnson Medical Inc. and Baxter Healthcare Corp.) and spunbond/meltblown/spunbond laminate materials (available from Kimberly-Clark Corp. and sold under the trademark Evolution™ Fabric System).

In an alternative embodiment, the present invention provides novel surgical drapes having tape attachment strips around a fenestration. The tape attachment strips provide a leak free perimeter seal between the patient being draped and the top surface of the drape. In addition, the tape attachment strips provide a landing surface to which an optional incise drape material may be attached.

The advantages of the present invention stem, in part, from the unique flow transition from the patient to the top of the drape as a result of the unique tape attachment strips which attach the drape to a patient's skin. Previous drape systems have relied on double-sided tape strips which connect the bottom surface of the drape fabric to the patient's skin. Unfortunately, it is very difficult to precisely align the edge of the double-sided tape with the edge of the drape fabric. As a result the non-adhered portion of drape fabric can inhibit fluid flow (e.g., directing the fluid along the edge of the double-sided tape) onto the top surface of the drape. The fluid can thus work to loosen the double-sided tape from the skin. Additional benefits are derived when the drapes of the present invention are used with incise drapes. Certain incise drapes comprise adhesives or chemicals which are incompatible with certain drape fabrics. For example, the direct adhesion of certain incise drapes to certain drape fabrics can ruin the drape fabric. This is particularly undesirable when the drape fabric is designed to be reused (e.g., a linen drape). In addition, certain incise drapes do not provide the desired level of adhesion to certain drape fabrics (e.g., either too little adhesion or too much adhesion). Using the tape attachment strips of the present invention solves these problems. In essence, the tape attachment strips provide a landing area where the incise material can be attached. This avoids any direct contact between the incise material and the drape fabric and allows uniform adhesive bonds regardless of the drape fabric employed. When the surgical procedure is finished the incise drape and tape attachment strips can be peeled off without damage to the drape fabric. In addition, when the tape attachment strip comprises a water-dispersible adhesive, the incise drape, tape attachment strips and drape fabric can be separated automatically by the laundry process.

Preferably, the entire drape system (including the tape attachment strips) should be capable of being sterilized. Several different sterilization processes are used in the medical field. For example, steam autoclave, gamma radiation, and ethylene oxide may be employed. Preferred drape systems should withstand at least one cycle through the desired sterilization process. For example, preferably the drape system should remain functional after irradiation with up to at least 25 kGys gamma cobalt-60 radiation, a dosage often used for sterilization of medical devices.

DETAILED DESCRIPTION OF THE DRAWINGS

Reference is made to the figures wherein like parts have been given like index numbers. Throughout the drawings the various layers of tape, adhesive, or liner have been exaggerated in thickness for purposes of illustration and clarity. In particular, the adhesive layer is shown in exaggerated thickness. In addition, the size of the various components may be modified, if desired, to accommodate the particular needs of the drape.

Figure 1B:
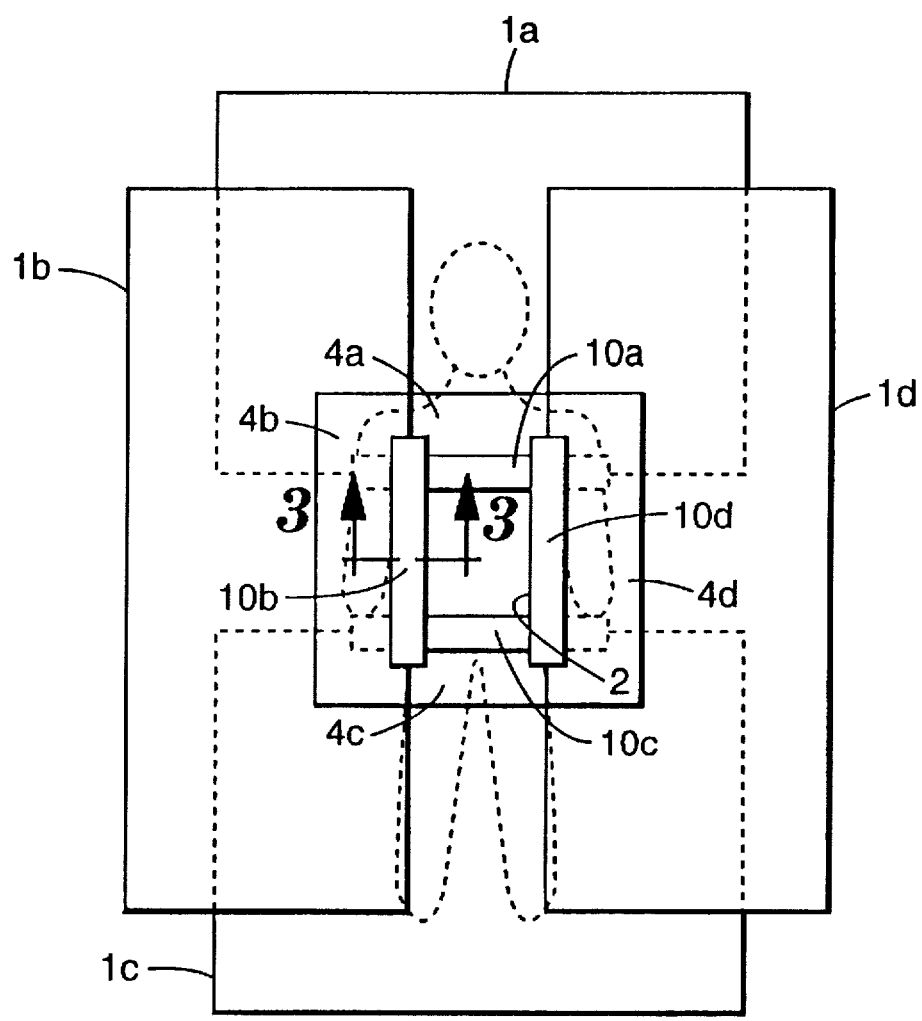

Referring to FIGS. 1a and 1b, there is shown a universal drape system of the present invention. FIG. 1a illustrates a universal drape system prior to assembly. FIG. 1b illustrates the same drape system after assembly. To aid in understanding the present invention a patient's chest is being depicted draped with a universal drape of the present invention. However, it is anticipated that other animals (e.g., horses, dogs, cats, etc.) or other objects could be draped in a like fashion. It is further anticipated that other surgical sites (i.e., other than the chest of a human) could be draped using the universal drape of the present invention. FIGS. 1a and 1b illustrate a four panel universal drape of the present invention. If desired one or more of the panels could be omitted (e.g., to construct a partial border along a surgical site) or additional panels can be included (e.g., to provide a polygon fenestration having more than four sides).

As shown in FIGS. 1a and 1b, the universal drape system comprises four drape panels (1a, 1b, 1c, and 1d) each having along at least a portion of one edge a tape attachment strip (10a, 10b, 10c, and 10d, respectively and a region of a fluid absorbing material (layers 4a, 4b, 4c, and 4d, respectively). To form a universal drape (thereby forming fenestration 2) the drape panels are arranged as shown in FIG. 1b. Preferably, two panels (head and foot panels) are arranged in parallel fashion, thus defining two sides of fenestration 2. Each panel is adhered to the patient's skin using the exposed adhesive portion of the tape attachment strip. The other two sides of the fenestration are formed using two additional panels. A portion of the tape attachment strip on the top two panels will contact the patient and a portion will overlap the underlying panels of the universal drape system. Alternatively, if so desired, the health care provided may choose to overlap the panels in a different order. For example, each side of the fenestration may be defined in any particular order. To best provide a leak free seam between the patient and the top of the drape system it is preferred that the tape attachment strips overlap (or at least abut) at the corners.

Figure 2A:
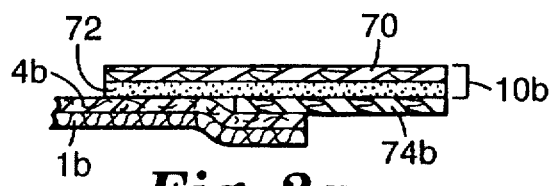
Figure 2B:
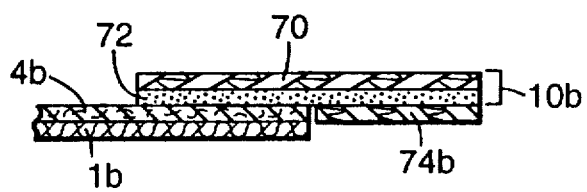
Figure 2C:
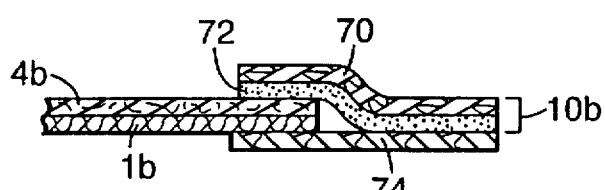

Referring to FIGS. 2a, 2b, and 2c, various alternative embodiments of the present invention are illustrated. In particular, three alternative methods of attaching the tape attachment strip to the drape panels are shown. In FIG. 2a, a particularly preferred embodiment is shown. Tape 10b comprises backing 70 and adhesive layer 72. Prior to attachment to the drape panel, the entire surface of adhesive layer 72 was preferably covered with a liner 74. A first portion 74a of the liner (not shown) is removed to expose a portion of adhesive layer 72. The exposed portion of adhesive layer is then contacted against the drape panel. In FIG. 2a, a portion of the drape panel overlaps the remaining portion 74b of the liner. This ensures that no portion of exposed adhesive is uncovered. Alternatively, as shown in FIG. 2b the remaining portion 74b of liner may butt up to the edge of the drape panel. Preferably, no gap or only a minimal gap between the edges of the drape panel and liner would exist. Also alternatively, and as shown in FIG. 2c, the tape attachment strip (comprising backing 70 and adhesive layer 72) is initially covered with a liner 74. Between a portion of the liner and the adhesive tape is placed the edge of the drape panel. This may be accomplished, for example, by peeling the tape from the liner, attaching the drape panel to a portion of the tape, and then re-attaching the liner to the tape. In all of the above embodiments, that portion of the liner which covers the adhesive layer of the tape is removed to expose the adhesive. The tape may then be placed against the patient's skin to secure the drape to the patient.

Figure 3:
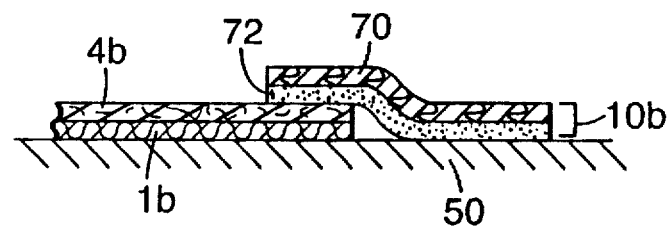
FIG. 3 is a cross-sectional view of the surgical drape system of FIG. 1b taken along line 3—3 of FIG. 1b.

FIG. 3 illustrates a cross-section of the drape system of the present invention along line 3—3 of FIG. 1b. As can be seen from this cross-section, the tape attachment strip provides a ramp over which fluid may easily flow. Notably, this cross-section is very much exaggerated in thickness. The actual tapes used in this invention are preferably much thinner in cross-section.

FIGS. 4 and 5 illustrate alternative embodiments of the drape panels of the present invention. In FIG. 4 a drape panel 1 is shown with a tape attachment strip 13 which extends along one edge of the panel and a region of a fluid absorbing material 4. Preferred panels for use in the present invention have tape attachment strips along at least a portion of the panel edge (i.e., along at least that portion of the drape edge which defines the fenestration. If desired, however, and as illustrated in FIG. 4 the tape attachment strip can be adhesively attached along the entire edge of the panel. In FIG. 5 a drape panel 1 is shown with a plurality of tape attachment strips (14a, 14b, and 14c) along one edge. For particularly large drape systems it is anticipate that having separate pieces of tape attachment strip will facilitate placement of the tape against the patient. The center piece of tape attachment strip 14b can be placed against the patient while the other two pieces still retain their liners. After the center piece is attached to the patient the other two pieces can be attached. Alternatively, (not shown) one might segment the liner of a full length tape attachment strip (as shown in FIG. 4) into a plurality of sections. Each section of liner could be sequentially removed to expose a portion of the adhesive surface. This technique is especially useful when the drape panel is quite long and where a continuous adhesive seal is desired along the whole edge of the panel.

Figure 6B:
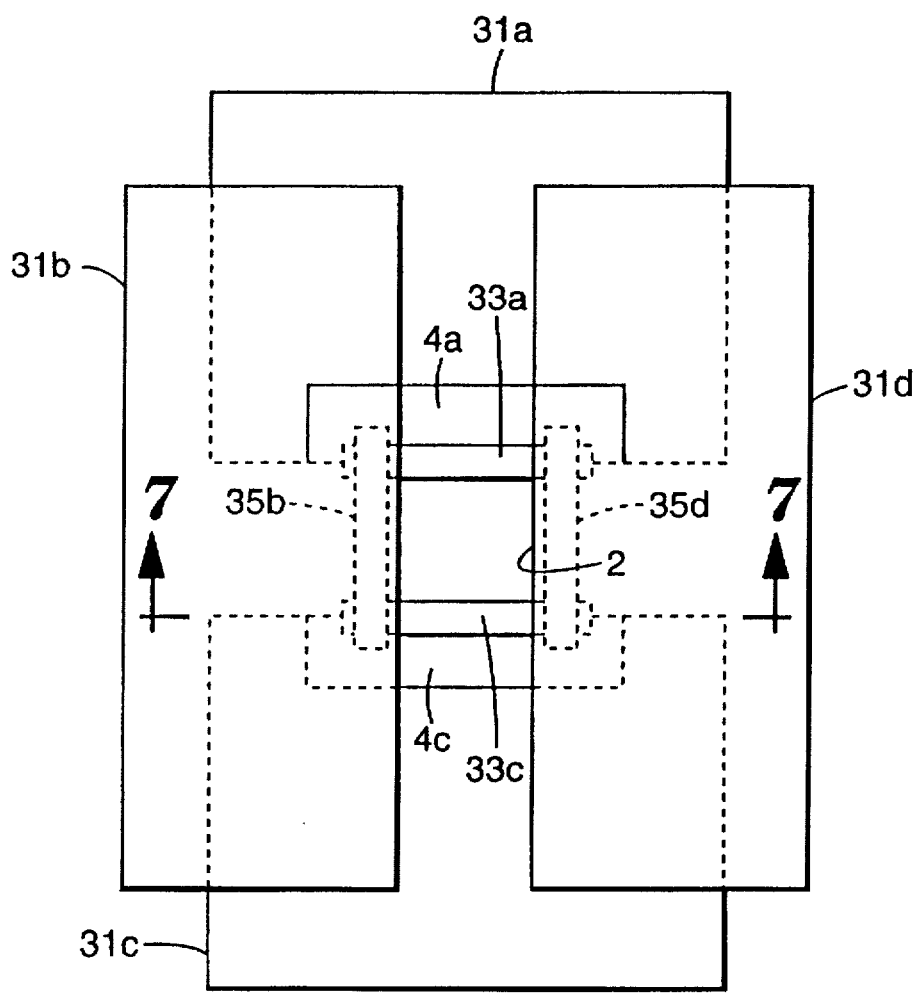
Figure 7:
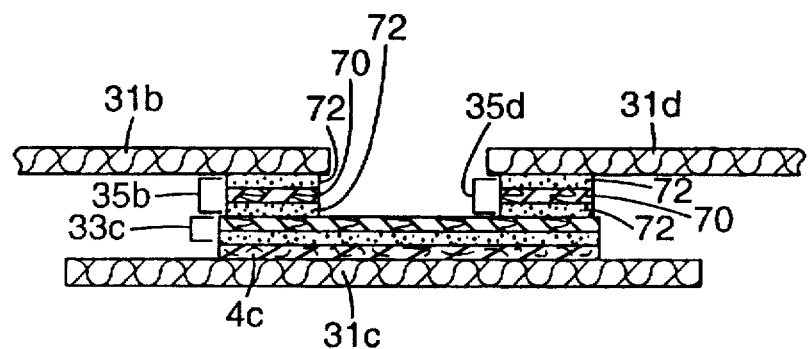
FIG. 7 is a cross-sectional view of the surgical drape system of FIG. 6b taken along line 7—7 of FIG. 6b.

FIGS. 6a, 6b, and 7 illustrate an alternative embodiment of the present invention. In this embodiment, two of the drape panels (31b and 31d) are provided with strips of a double-sided adhesive tape (35b and 35d, respectively) rather than a single sided adhesive tape. Suitable double-sided adhesive tapes for use in this invention include the double-sided adhesive tapes disclosed in U.S. patent application Ser. No. 08/208,990, filed on Mar. 10, 1994, which is herein incorporated by reference. In use, drape panels 31a and 31c are placed against the patient using single-sided tape attachment strips 33a and 33c, respectively. Drape panels 31b and 31d are then placed over the patient and overlapping panels 31a and 31c. Normally the use of a double-sided tape on a universal drape panel would pose flow problems for any fluids emanating from the surgical site. However, when the universal drape is constructed in this fashion any fluids unable to flow over edges 37b and 37d are merely channeled over tape attachment strip 33a or 33c and onto the top surface of panel 31a or 31c. Thus, in contrast to a universal drape comprising four panels each having double-sided tapes, no fluid will leak under the panels and not be directed to the top surface of a panel.

FIG. 7 illustrates a cross-section of the drape system of the present invention along line 7—7 of FIG. 6b. As can be seen from this cross-section, the double-sided tapes (35b and 35d) inhibit fluid flow onto the top surface of panels 31b and 31d. However, the fluid can run parallel to the double-sided tape and onto the top surface of panels 31a or 31c.

Figure 8:
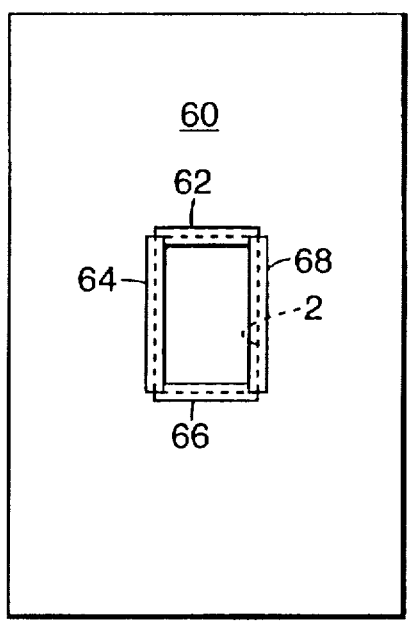
FIG. 8 is a top plan view of a surgical drape of the present invention having a fenestration and strips of adhesive tape peripherally surrounding the fenestration.
Figure 12:
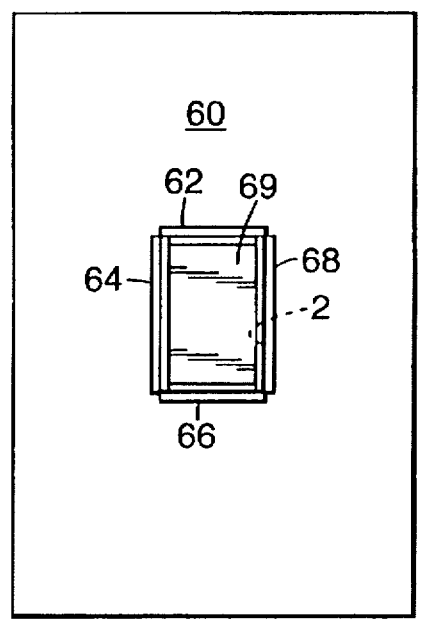
FIG. 12 is a top plan view of a surgical drape of the present invention having a fenestration and strips of adhesive tape peripherally surrounding the fenestration and further comprising an incise drape attached to the top surface of the strips of adhesive tape.

FIG. 8 illustrates a general purpose surgical drape of the present invention comprising a fabric sheet 60 having a rectangular fenestration therein. On each edge of the fenestration is attached a tape attachment strip (62, 64, 66 and 68). Prior to use, the tape attachment strips are attached to the drape fabric in the manner depicted in FIGS. 2a, 2b or 2c. In use, the tape attachment strips provide a ramp over which fluid may easily flow as depicted on FIG. 3. To best provide a leak free seam between the patient and the top of the drape it is preferred that the tape attachment strips overlap (or at least abut) at the corners. The drape depicted in FIG. 8 may be easily assembled by the manufacturer. Four pieces of adhesive tape (preferably having a slit liner as previously described) are cut approximately to the length of the edges of the fenestration. A portion of the liner is removed from the tape thus exposing a strip of adhesive down the length of the tape. The adhesive portion is placed against the edge of the drape at the fenestration leaving a lined portion of tape overhanging the fenestration. In use the remaining portion of liner is removed and the tape pressed against the patient.

The top surfaces of the tape attachment strips provide a landing zone where an additional and optional incise drape may be adhesively attached.

Figure 10A:
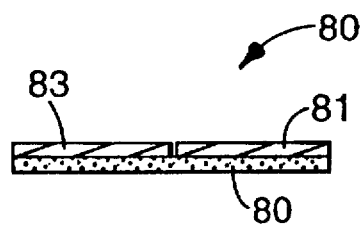
FIGS. 10a, 10b, and 10c are side views of the tape attachment strip of FIG. 9 taken along lines 10a—10a, 10b—10b, and 10c—10c, respectively.
Figure 10B:
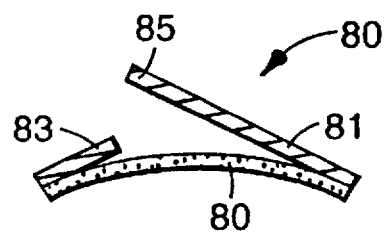
Figure 10C:
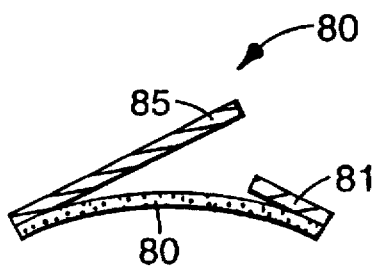

FIG. 9 depicts the liner side an alternative tape attachment strip of the present invention. The tape attachment strip 80 has a two-piece liner attached to the adhesive side of the tape. The liner pieces 81 and 83 are separated along a sinusoidal line 82. When the tape is flexed in the manner depicted in FIGS. 10b and 10c, a portion 85 of the preferably somewhat stiffer liner separates from the adhesive tape and provides tabs which may be grasped by a user, thus facilitating the peeling of the liner from the tape. FIG. 10a illustrates a cross-section of the tape attachment strip of FIG. 9 prior to the tape being flexed. FIGS. 10b and 10c illustrate the cross-sections of the tape attachment strip along line B—B and C—C of FIG. 9 when the tape is being flexed. Notably, that portion of the liner 85 which crosses the midline of the tape separates from the tape when the tape is flexed.

Figure 11A:
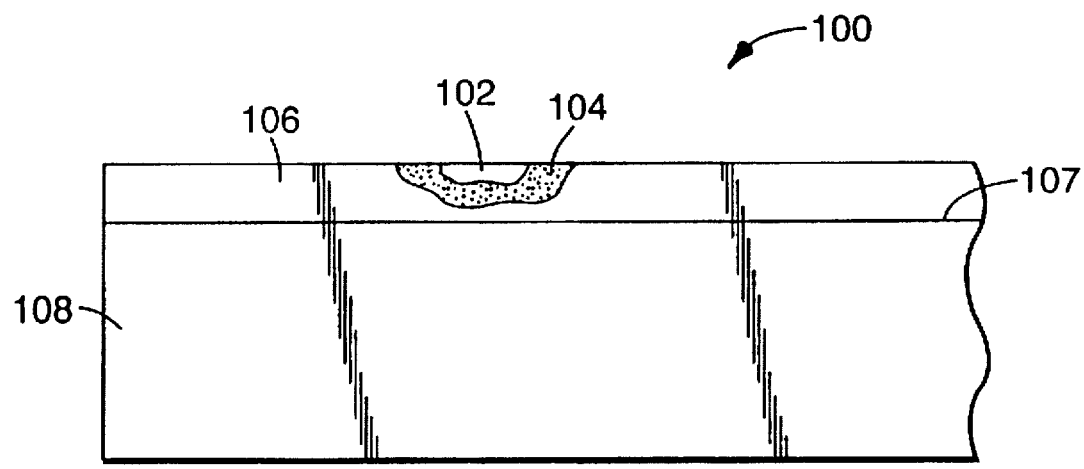
FIGS. 11a and 11b are plan views of the liner side of a presently preferred tape attachment strip of the present invention, wherein the liner has been slit lengthwise and a portion of the tape and liner have been folded to facilitate removal of the liner from the tape during use.
Figure 11B:
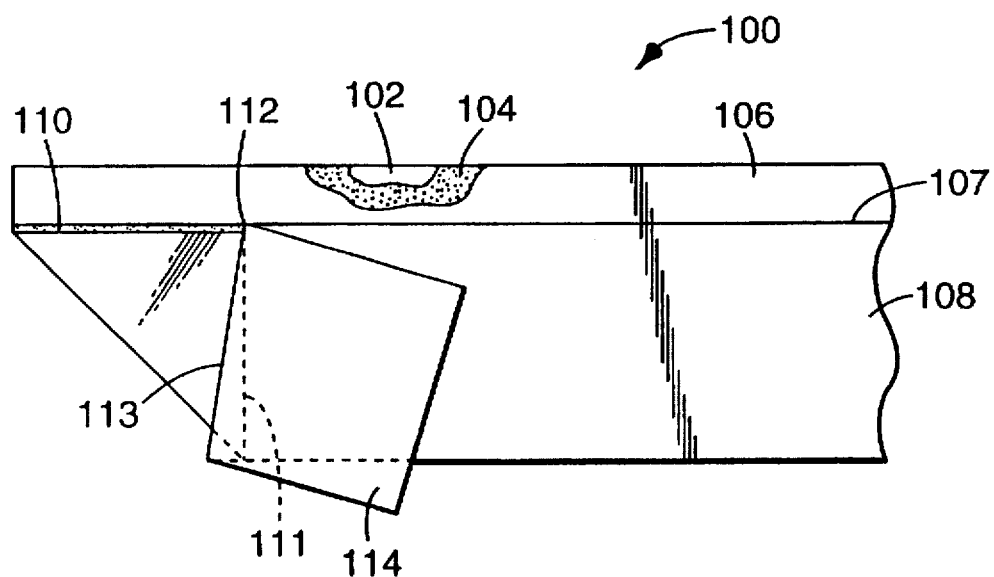

FIGS. 11a and 11b depicts the liner side of a presently preferred tape attachment strip of the present invention. The tape attachment strip 100 has a two-piece liner attached to the adhesive side of the tape (shown in cutaway as backing 102 and adhesive layer 104). The liner pieces 106 and 108 are separated along line 107. Liner piece 106 is generally removed by the manufacturer when the tape attachment strip is attached to a drape or drape panel. To facilitate removal of liner piece 108 by the health care provider, the manufacturer may create a "tab" of liner 114 by separating the liner from the tape at the end of the tape and folding the adhesive tape as depicted in FIG. 11b. Preferably, a corner of the adhesive tape is folded onto itself (e.g., positioning edge 110 parallel to slit 107), thereby covering a portion of the exposed adhesive. Liner 108 is preferably folded back on itself thereby creating crease line 113, wherein one end 112 of crease line 113 is positioned, preferably, to just overlap edge 111 of the folded tape corner. Preferably, liner 108 is folded in a manner such that crease line 113 and slit 107 form an angle between 45 and 80 degrees. This angled fold facilitates the peeling of liner 108 without tearing the liner. More preferably, crease line 113 and slit 107 form an angle between 60 and 75 degrees.

The following examples are offered to aid in the understanding of the present invention and are not to be construed as limiting the scope thereof. Unless otherwise indicated, all parts and percentages are by weight.

EXAMPLES

Example 1

Universal Surgical Drape System with Tape Attachment Strips

A universal surgical drape kit is produced in the following manner. Four panels of drape material (available from E.I. Du Pont de Nemours Co. as Sontara™ 8018) are fitted with tape attachment strips as depicted in FIG. 1a and as herein described. The universal drape kit comprises two side panels measuring approximately 2 m by 1 m, and two end panels measuring approximately 1.2 m by 1 m. Each panel is fitted with a fluid absorbing material along one edge. The fluid absorbing materials (measuring 0.3 m by 0.6 m) are applied to the top surface of each drape panel. Along a center portion of the edge of the drape panels is applied, as herein described, a 0.5 m long piece of a commercially available single-sided adhesive tape (available from 3M Co., St. Paul, Minn. as No. 1526SL transparent 0.13 mm polyethylene medical tape). This adhesive tape measures 50.8 mm in width and has a liner covering the adhesive side of the tape. The liner has been slit into two narrower strips of material (measuring approximately 12 and 47.8 mm, respectively). The narrower strip of liner is removed by peeling the liner from the adhesive and the exposed adhesive is placed against the topside of the fluid absorbing material along the edge of the panel. A portion of the wide strip of liner overlaps the edge of the panel by up to about 3 mm.

In use, the wide strip of liner is removed thus exposing the rest of the adhesive. The exposed adhesive may then be placed against the patient to which the drape panel is being attached. The other panels are then similarly attached to the patient. In a preferred use, the four panels are arranged to form a rectangular fenestration having a perimeter defined by the tape attachment strips. When the universal drape is so formed, fluid is able to easily flow across the tape and onto the fluid absorbing material.

Example 2

Universal Surgical Drape System with Tape Attachment Strips

A universal surgical drape is produced in a manner similar to that used in Example 1 except that the side drape panels are fitted with three 0.5 m long tape attachment strips along the edge of the panel in place of the single tape strip. This construction is illustrated in FIG. 5. In use, the center tape attachment strip is applied against the patient while the other two strips still retain their respective liners. Once the first center strip is securely attached to the patient the other two strips may be applied to the patient. This avoids having to handle a very long piece of tape in one application. The other panels are then attached to the patient. In a preferred use, the four panels are arranged to form a rectangular fenestration having a perimeter defined by the center tape attachment strips. When the universal drape is so formed, fluid is able to easily flow across the tape and onto the fluid absorbing material.

Example 3

Universal Surgical Drape System with Tape Attachment Strips

A universal surgical drape is produced in a manner similar to that used in Example 1 except that the side drape panels are fitted with a 1.5 m long tape attachment strips along the edge of the panel in place of the shorter tape strip. This construction is illustrated in FIG. 4. The liner of the long tape attachment strips is segmented into three shorter sections. In use, the center liner portion of the long tape attachment strip is applied against the patient while the other two liner portions remain in place against the adhesive. Once the first center portion of the tape attachment strip is securely attached to the patient the other two portions of liner may be removed and the exposed adhesive applied to the patient. This avoids having to handle a very long piece of exposed tape in one application. The other panels are then attached to the patient. In a preferred use, the four panels are arranged to form a rectangular fenestration having a perimeter defined by the tape attachment strips. When the universal drape is so formed, fluid is able to easily flow across the tape and onto the fluid absorbing material.

Example 4

Fenestrated Surgical Drape with Tape Attachment Strips

A fenestrated surgical drape is produced in the following manner. A rectangular sheet of drape material having a rectangular fenestration is fitted with four tape attachment strips as depicted in FIG. 8 and as herein described. Along the edge of the drape fenestration is applied, as herein described, four pieces of a commercially available single-sided adhesive tape (available from 3M Co., St. Paul, Minn. as No. 1526SL transparent 0.13 mm polyethylene medical tape). This adhesive tape measures 50.8 mm in width and has a liner covering the adhesive side of the tape. The liner has been slit into two narrower strips of material (measuring approximately 12 and 47.8 mm, respectively). The narrower strip of liner is removed by peeling the liner from the adhesive and the exposed adhesive is placed against the topside of the drape along the edge of the fenestration. A portion of the wide strip of liner overlapsthe edge of the drape fabric by up to about 3 mm.

In use, the wide strip of liner is removed thus exposing the rest of the adhesive. The exposed adhesive may then be placed against the patient to which the drape is being attached. The other three pieces of tape attachment strips are similarly applied. When the drape is so formed, fluid is able to easily flow across the tape and onto the fluid absorbing material.

Example 5

Fenestrated Surgical Drape with Tape Attachment Strips

An alternative fenestrated surgical drape was produced in the following manner. A commercial transverse laparotomy drape (available as BARRIER #1282 transverse laparotomy drape from Johnson & Johnson Medical Inc., Arlington, Tex.) was modified by cutting away the double-sided adhesive tape strips which border the fenestration. The double-sided adhesive tape strips had been attached to a piece of plastic film which was sealed to the drape fabric (i.e., between the drape fabric itself and a second layer of an absorbent material). The double-sided tape was completely removed as was that part of the plastic film which extended past the rectangular fenestration. This left a fenestration measuring approximately 155 mm by 380 mm. Along the edges of the fenestration was applied, as herein described, four pieces of a commercially available single-sided adhesive tape (available from 3M Co., St. Paul, Minn. as No. 1526SL transparent 0.13 mm polyethylene medical tape). This adhesive tape measures 50.8 mm in width and has a liner covering the adhesive side of the tape. The liner has been slit into two narrower strips of material (measuring approximately 12 and 47.8 mm, respectively). As depicted in FIG. 11b, at least one end of each of the four pieces of tape was folded to provide convenient finger tabs of liner. The narrower strip of liner was then removed by peeling the liner from the adhesive and the exposed adhesive was placed against the topside of the drape along the edge of the fenestration. A portion of the wide strip of liner overlapped the edge of the drape fabric by about 3 mm.

In use, the wide strip of liner is removed (e.g., by grabbing the finger tab of liner and peeling the liner from the tape) thus exposing the rest of the adhesive. The exposed adhesive may then be placed against the patient to which the drape is being attached. The other three pieces of tape attachment strips are similarly applied. When the drape is so formed, fluid is able to easily flow across the tape and onto the fluid absorbing material.

Various modifications and alterations of this invention will be apparent to those skilled in the art without departing from the scope and spirit of this invention, and it should be understood that this invention is not limited to the illustrative embodiments set forth herein.

What is claimed is:

1. A universal surgical drape, comprising:

four surgical drape panels each having a top surface and a bottom surface; and four tape attachment strips comprising a backing and a pressure sensitive adhesive layer covering one side of said backing, wherein a first portion of said tape attachment strips is adhesively attached to the top surface and along at least a portion of one edge of said drape panels and a second portion of said tape attachment strips overhangs said drape panels, wherein said four drape panels are overlapped so as to form a larger sheet having a rectangular fenestration, wherein said tape attachment strips form the perimeter of said fenestration, wherein at least a portion of the exposed adhesive portion of at least two of said tape attachment strips overlaps and contacts the top surface of an underlying tape attachment strip thereby defining corners of the fenestration, and wherein said drape, when placed against a patient, provides a leak free seal between the patient and the top surface of the drape along the corners and edges of the fenestration.

2. The universal surgical drape of claim 1, wherein said drape panels comprise a reusable fabric.

3. The universal surgical drape of claim 1, wherein said drape panels comprise a disposable fabric.

4. A surgical drape, comprising:

a sheet of surgical drape fabric having a rectangular fenestration cut therein; and four tape attachment strips comprising a backing, an adhesive layer covering one side of said backing, and a liner, wherein said tape attachment strips are adhesively attached to the top surface of said sheet along the edges of said fenestration, wherein a second portion of said tape attachment strips overhangs the fenestration of said drape and is covered with said liner, and wherein said tape attachment strips overlap at the corners of said fenestration and said drape, when placed against a patient, provides a leak free seal between the patient and the top surface of the drape along the corners and edges of the fenestration.

5. The surgical drape of claim 4, wherein said sheet of drape fabric further comprise a layer of fluid absorbing material near the fenestration, and wherein said tape attachment strip is adhesively attached to the top surface of said fluid absorbing material.

6. The surgical drape of claim 4, wherein said drape fabric is a reusable fabric.

7. The surgical drape of claim 4, wherein said drape fabric is a disposable fabric.

8. The surgical drape of claim 4, which, when in use during a surgical procedure, further comprises an incise drape attached to the top surface of said tape attachment strips.

9. The surgical drape of claim 8, wherein said adhesive layer comprises a water-dispersible pressure sensitive adhesive.

* * * * *